US008908877B2

(12) United States Patent
Abdollahzadeh Milani et al.

(10) Patent No.: US 8,908,877 B2
(45) Date of Patent: Dec. 9, 2014

(54) EAR-COUPLING DETECTION AND ADJUSTMENT OF ADAPTIVE RESPONSE IN NOISE-CANCELING IN PERSONAL AUDIO DEVICES

(75) Inventors: Ali Abdollahzadeh Milani, Austin, TX (US); Gautham Devendra Kamath, Austin, TX (US)

(73) Assignee: Cirrus Logic, Inc., Austin, TX (US)

( * ) Notice: Subject to any disclaimer, the term of this patent is extended or adjusted under 35 U.S.C. 154(b) by 593 days.

(21) Appl. No.: 13/310,380

(22) Filed: Dec. 2, 2011

(65) Prior Publication Data

US 2012/0207317 A1 Aug. 16, 2012

Related U.S. Application Data

(60) Provisional application No. 61/419,532, filed on Dec. 3, 2010, provisional application No. 61/493,162, filed on Jun. 3, 2011.

(51) Int. Cl.
*A61F 11/06* (2006.01)
*G10K 11/178* (2006.01)

(52) U.S. Cl.
CPC ...... *G10K 11/1784* (2013.01); *G10K 2210/108* (2013.01); *G10K 2210/3039* (2013.01); *G10K 2210/3055* (2013.01); *G10K 2210/503* (2013.01)
USPC ...... 381/71.1; 381/71.6; 381/71.8; 381/71.11

(58) Field of Classification Search
USPC .......... 381/13, 71.1, 71.6, 71.8, 71.11, 71.14, 381/73.1, 93, 94.1–94.9, 317; 700/94
See application file for complete search history.

(56) References Cited

U.S. PATENT DOCUMENTS 5,251,263 A 10/1993 Andrea et al.
5,337,365 A 8/1994 Hamabe et al.
5,410,605 A 4/1995 Sawada et al.

(Continued)

FOREIGN PATENT DOCUMENTS

EP 1880699 A2 1/2008
EP 2395500 A1 12/2011

(Continued)

OTHER PUBLICATIONS

U.S. Appl. No. 14/029,159, filed Sep. 17, 2013, Li, et al.

(Continued)

*Primary Examiner* — Vivian Chin
*Assistant Examiner* — Friedrich W Fahnert
(74) *Attorney, Agent, or Firm* — Mitch Harris, Atty at Law, LLC; Andrew M. Harris

(57) ABSTRACT

A personal audio device, such as a wireless telephone, includes an adaptive noise canceling (ANC) circuit that adaptively generates an anti-noise signal from a reference microphone signal and injects the anti-noise signal into the speaker or other transducer output to cause cancellation of ambient audio sounds. An error microphone is also provided proximate the speaker to estimate an electro-acoustical path from the noise canceling circuit through the transducer. A processing circuit determines a degree of coupling between the user's ear and the transducer and adjusts the adaptive cancellation of the ambient sounds to prevent erroneous and possibly disruptive generation of the anti-noise signal if the degree of coupling lies either below or above a range of normal operating ear contact pressure.

30 Claims, 7 Drawing Sheets

(56) References Cited

U.S. PATENT DOCUMENTS

| | | | |
|---|---|---|---|
| 5,425,105 | A | 6/1995 | Lo et al. |
| 5,586,190 | A | 12/1996 | Trantow et al. |
| 5,640,450 | A | 6/1997 | Watanabe |
| 5,699,437 | A | 12/1997 | Finn |
| 5,706,344 | A | 1/1998 | Finn |
| 5,768,124 | A | 6/1998 | Stothers et al. |
| 5,815,582 | A | 9/1998 | Claybaugh et al. |
| 5,946,391 | A | 8/1999 | Dragwidge et al. |
| 5,991,418 | A | 11/1999 | Kuo |
| 6,041,126 | A | 3/2000 | Terai et al. |
| 6,118,878 | A | 9/2000 | Jones |
| 6,219,427 | B1 | 4/2001 | Kates et al. |
| 6,418,228 | B1 | 7/2002 | Terai et al. |
| 6,434,246 | B1 | 8/2002 | Kates et al. |
| 6,434,247 | B1 | 8/2002 | Kates et al. |
| 6,768,795 | B2 | 7/2004 | Feltstrom et al. |
| 6,850,617 | B1 | 2/2005 | Weigand |
| 7,103,188 | B1 | 9/2006 | Jones |
| 7,181,030 | B2 | 2/2007 | Rasmussen et al. |
| 7,330,739 | B2 | 2/2008 | Somayajula |
| 7,365,669 | B1 | 4/2008 | Melanson |
| 7,742,790 | B2 | 6/2010 | Konchitsky et al. |
| 8,019,050 | B2 | 9/2011 | Mactavish et al. |
| 8,249,262 | B2 | 8/2012 | Chua et al. |
| 8,290,537 | B2 | 10/2012 | Lee et al. |
| 8,379,884 | B2 | 2/2013 | Horibe et al. |
| 8,401,200 | B2 | 3/2013 | Tiscareno et al. |
| 2001/0053228 | A1 | 12/2001 | Jones |
| 2002/0003887 | A1 | 1/2002 | Zhang et al. |
| 2004/0165736 | A1 | 8/2004 | Hetherington et al. |
| 2004/0167777 | A1 | 8/2004 | Hetherington et al. |
| 2004/0264706 | A1 | 12/2004 | Ray et al. |
| 2005/0117754 | A1 | 6/2005 | Sakawaki |
| 2005/0240401 | A1 | 10/2005 | Ebenezer |
| 2006/0153400 | A1 | 7/2006 | Fujita et al. |
| 2007/0030989 | A1 | 2/2007 | Kates |
| 2007/0033029 | A1 | 2/2007 | Sakawaki |
| 2007/0038441 | A1 | 2/2007 | Inoue et al. |
| 2007/0053524 | A1 | 3/2007 | Haulick et al. |
| 2007/0076896 | A1* | 4/2007 | Hosaka et al. ............. 381/71.11 |
| 2007/0154031 | A1 | 7/2007 | Avendano et al. |
| 2007/0258597 | A1 | 11/2007 | Rasmussen et al. |
| 2007/0297620 | A1 | 12/2007 | Choy |
| 2008/0019548 | A1 | 1/2008 | Avendano |
| 2008/0181422 | A1 | 7/2008 | Christoph |
| 2008/0226098 | A1 | 9/2008 | Haulick et al. |
| 2009/0012783 | A1 | 1/2009 | Klein |
| 2009/0034748 | A1 | 2/2009 | Sibbald |
| 2009/0041260 | A1 | 2/2009 | Jorgensen et al. |
| 2009/0046867 | A1 | 2/2009 | Clemow |
| 2009/0196429 | A1 | 8/2009 | Ramakrishnan et al. |
| 2009/0220107 | A1 | 9/2009 | Every et al. |
| 2009/0238369 | A1 | 9/2009 | Ramakrishnan et al. |
| 2009/0245529 | A1 | 10/2009 | Asada et al. |
| 2009/0254340 | A1 | 10/2009 | Sun et al. |
| 2009/0290718 | A1 | 11/2009 | Kahn et al. |
| 2009/0296965 | A1 | 12/2009 | Kojima |
| 2009/0304200 | A1 | 12/2009 | Kim et al. |
| 2010/0014683 | A1 | 1/2010 | Maeda et al. |
| 2010/0014685 | A1 | 1/2010 | Wurm |
| 2010/0061564 | A1 | 3/2010 | Clemow et al. |
| 2010/0069114 | A1 | 3/2010 | Lee et al. |
| 2010/0082339 | A1 | 4/2010 | Konchitsky et al. |
| 2010/0098263 | A1 | 4/2010 | Pan et al. |
| 2010/0124335 | A1 | 5/2010 | Wessling et al. |
| 2010/0124336 | A1 | 5/2010 | Shridhar et al. |
| 2010/0166203 | A1 | 7/2010 | Peissig et al. |
| 2010/0195838 | A1 | 8/2010 | Bright |
| 2010/0195844 | A1 | 8/2010 | Christoph et al. |
| 2010/0272283 | A1 | 10/2010 | Carreras et al. |
| 2010/0274564 | A1 | 10/2010 | Bakalos et al. |
| 2010/0296666 | A1 | 11/2010 | Lin |
| 2010/0296668 | A1 | 11/2010 | Lee et al. |
| 2010/0310086 | A1 | 12/2010 | Magrath et al. |
| 2010/0322430 | A1 | 12/2010 | Isberg |
| 2011/0007907 | A1 | 1/2011 | Park et al. |
| 2011/0106533 | A1 | 5/2011 | Yu |
| 2011/0142247 | A1 | 6/2011 | Fellers et al. |
| 2011/0144984 | A1 | 6/2011 | Konchitsky |
| 2011/0158419 | A1 | 6/2011 | Theverapperuma et al. |
| 2011/0222698 | A1 | 9/2011 | Asao et al. |
| 2011/0249826 | A1 | 10/2011 | Van Leest |
| 2011/0288860 | A1 | 11/2011 | Schevciw et al. |
| 2011/0293103 | A1 | 12/2011 | Park et al. |
| 2011/0299695 | A1 | 12/2011 | Nicholson |
| 2011/0317848 | A1 | 12/2011 | Ivanov et al. |
| 2012/0135787 | A1 | 5/2012 | Kusunoki et al. |
| 2012/0140943 | A1 | 6/2012 | Hendrix et al. |
| 2012/0250873 | A1 | 10/2012 | Bakalos et al. |
| 2012/0259626 | A1 | 10/2012 | Li et al. |
| 2012/0300958 | A1 | 11/2012 | Klemmensen |
| 2012/0308021 | A1 | 12/2012 | Kwatra et al. |
| 2012/0308024 | A1 | 12/2012 | Alderson et al. |
| 2012/0308025 | A1 | 12/2012 | Hendrix et al. |
| 2012/0308026 | A1 | 12/2012 | Kamath et al. |
| 2012/0308027 | A1 | 12/2012 | Kwatra |
| 2012/0308028 | A1 | 12/2012 | Kwatra et al. |
| 2012/0310640 | A1 | 12/2012 | Kwatra et al. |
| 2013/0010982 | A1 | 1/2013 | Elko et al. |
| 2013/0243225 | A1 | 9/2013 | Yokota |
| 2013/0272539 | A1 | 10/2013 | Kim et al. |
| 2013/0287218 | A1 | 10/2013 | Alderson et al. |
| 2013/0287219 | A1 | 10/2013 | Hendrix et al. |
| 2013/0301842 | A1 | 11/2013 | Hendrix et al. |
| 2013/0301846 | A1 | 11/2013 | Alderson et al. |
| 2013/0301847 | A1 | 11/2013 | Alderson et al. |
| 2013/0301848 | A1 | 11/2013 | Zhou et al. |
| 2013/0301849 | A1 | 11/2013 | Alderson et al. |
| 2013/0343556 | A1 | 12/2013 | Bright |
| 2013/0343571 | A1 | 12/2013 | Rayala et al. |
| 2014/0044275 | A1 | 2/2014 | Goldstein et al. |
| 2014/0050332 | A1 | 2/2014 | Nielsen et al. |
| 2014/0177851 | A1 | 6/2014 | Kitazawa et al. |

FOREIGN PATENT DOCUMENTS

| | | | |
|---|---|---|---|
| GB | 2401744 | A | 11/2004 |
| GB | 2455821 | A | 6/2009 |
| GB | 2455824 | A | 6/2009 |
| GB | 2455828 | A | 6/2009 |
| JE | H06-186985 | A | 7/1994 |
| WO | WO 2003/015074 | A1 | 2/2003 |
| WO | WO 2007007916 | A1 | 1/2007 |
| WO | WO 2007113487 | A1 | 11/2007 |
| WO | WO 2010117714 | A1 | 10/2010 |
| WO | WO 2012134874 | A1 | 10/2012 |

OTHER PUBLICATIONS

U.S. Appl. No. 14/062,951, filed Oct. 25, 2013, Zhou, et al.
U.S. Appl. No. 13/968,007, filed Aug. 15, 2013, Hendrix, et al.
U.S. Appl. No. 13/686,353, filed Nov. 27, 2012, Hendrix, et al.
U.S. Appl. No. 13/795,160, filed Mar. 12, 2013, Hendrix, et al.
U.S. Appl. No. 13/692,367, filed Dec. 3, 2012, Alderson, et al.
U.S. Appl. No. 13/722,119, filed Dec. 20, 2012, Hendrix, et al.
U.S. Appl. No. 13/727,718, filed Dec. 27, 2012, Alderson, et al.
U.S. Appl. No. 13/784,018, filed Mar. 4, 2013, Alderson, et al.
U.S. Appl. No. 13/787,906, filed Mar. 7, 2013, Alderson, et al.
U.S. Appl. No. 13/729,141, filed Dec. 28, 2012, Zhou, et al.
U.S. Appl. No. 13/794,931, filed Mar. 12, 2013, Lu, et al.
U.S. Appl. No. 13/794,979, filed Mar. 12, 2013, Alderson, et al.
Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.
Toochinda, et al. "A Single-Input Two-Output Feedback Formulation for ANC Problems," Proceedings of the 2001 American Control Conference, Jun. 2001, pp. 923-928, vol. 2, Arlington, VA.
Kuo, et al., "Active Noise Control: A Tutorial Review," Proceedings of the IEEE, Jun. 1999, pp. 943-973, vol. 87, No. 6, IEEE Press, Piscataway, NJ.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.

(56) References Cited

OTHER PUBLICATIONS

Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.
Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
U.S. Appl. No. 14/228,322, filed Mar. 28, 2014, Alderson, et al.
U.S. Appl. No. 13/762,504, filed Feb. 8, 2013, Abdollahzadeh Milani, et al.
U.S. Appl. No. 13/721,832, filed Dec. 20, 2012, Lu, et al.
U.S. Appl. No. 13/724,656, filed Dec. 21, 2012, Lu, et al.
U.S. Appl. No. 14/252,235, filed Apr. 14, 2014, Lu, et al.
U.S. Appl. No. 13/968,013, filed Aug. 15, 2013, Abdollahzadeh Milani, et al.
U.S. Appl. No. 13/924,935, filed Jun. 24, 2013, Hellman.
U.S. Appl. No. 13/896,526, filed May 17, 2013, Naderi.
U.S. Appl. No. 14/101,955, filed Dec. 10, 2013, Alderson.
U.S. Appl. No. 14/101,777, filed Dec. 10, 2013, Alderson et al.
Abdollahzadeh Milani, et al., "On Maximum Achievable Noise Reduction in ANC Systems", 2010 IEEE International Conference on Acoustics Speech and Signal Processing, Mar. 14-19, 2010, pp. 349-352, Dallas, TX, US.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.
Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.
Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.
Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.
Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.
Kuo, et al., "Residual noise shaping technique for active noise control systems", J. Acoust. Soc. Am. 95 (3), Mar. 1994, pp. 1665-1668.
Lopez-Caudana, Edgar Omar, "Active Noise Cancellation: The Unwanted Signal and the Hybrid Solution", Adaptive Filtering Applications, Dr. Lino Garcia (Ed.), Jul. 2011, pp. 49-84, ISBN: 978-953-307-306-4, InTech.
Senderowicz, et al., "Low-Voltage Double-Sampled Delta-Sigma Converters", IEEE Journal on Solid-State Circuits, Dec. 1997, pp. 1907-1919, vol. 32, No. 12, Piscataway, NJ.
Hurst, et al., "An improved double sampling scheme for switched-capacitor delta-sigma modulators", 1992 IEEE Int. Symp. on Circuits and Systems, May 10-13, 1992, vol. 3, pp. 1179-1182, San Diego, CA.
U.S. Appl. No. 14/197,814, filed Mar. 5, 2014, Kaller, et al.
U.S. Appl. No. 14/210,537, filed Mar. 14, 2014, Abdollahzadeh Milani, et al.
U.S. Appl. No. 14/210,589, filed Mar. 14, 2014, Abdollahzadeh Milani, et al.
Black, John W., "An Application of Side-Tone in Subjective Tests of Microphones and Headsets", Project Report No. NM 001 064.01.20, Research Report of the U.S. Naval School of Aviation Medicine, Feb. 1, 1954, 12 pages (pp. 1-12 in pdf), Pensacola, FL, US.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.
Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.
Liu, et al., "Compensatory Responses to Loudness-shifted Voice Feedback During Production of Mandarin Speech", Journal of the Acoustical Society of America, Oct. 2007, pp. 2405-2412, vol. 122, No. 4.
Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.
Therrien, et al., "Sensory Attenuation of Self-Produced Feedback: The Lombard Effect Revisited", PLOS ONE, Nov. 2012, pp. 1-7, vol. 7, Issue 11, e49370, Ontario, Canada.
Campbell, Mikey, "Apple looking into self-adjusting earbud headphones with noise cancellation tech", Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noise-cancellation-tech.
Jin, et al. "A simultaneous equation method-based online secondary path modeling algorithm for active noise control", Journal of Sound and Vibration, Apr. 25, 2007, pp. 455-474, vol. 303, No. 3-5, London, GB.
Erkelens, et al., "Tracking of Nonstationary Noise Based on Data-Driven Recursive Noise Power Estimation", IEEE Transactions on Audio Speech and Language Processing, Aug. 2008, pp. 1112-1123, vol. 16, No. 6, Piscataway, NJ, US.
Rao, et al., "A Novel Two State Single Channel Speech Enhancement Technique", India Conference (INDICON) 2011 Annual IEEE, IEEE, Dec. 2011, 6 pages (pp. 1-6 in pdf), Piscataway, NJ, US.
Rangachari, et al., "A noise-estimation algorithm for highly non-stationary environments", Speech Communication, Feb. 2006, pp. 220-231, vol. 48, No. 2. Elsevier Science Publishers.

* cited by examiner

EAR-COUPLING DETECTION AND ADJUSTMENT OF ADAPTIVE RESPONSE IN NOISE-CANCELING IN PERSONAL AUDIO DEVICES

This U.S. Patent Application Claims priority under 35 U.S.C. 119(e) to U.S. Provisional Patent Application Ser. No. 61/419,532 filed on Dec. 3, 2010 and to U.S. Provisional Patent Application Ser. No. 61/493,162 filed on Jun. 3, 2011.

BACKGROUND OF THE INVENTION

1. Field of the Invention

The present invention relates generally to personal audio devices such as wireless telephones that include adaptive noise cancellation (ANC), and more specifically, to management of ANC in a personal audio device that is responsive to the quality of the coupling of the output transducer of the personal audio device to the user's ear.

2. Background of the Invention

Wireless telephones, such as mobile/cellular telephones, cordless telephones, and other consumer audio devices, such as mp3 players, are in widespread use. Performance of such devices with respect to intelligibility can be improved by providing noise canceling using a microphone to measure ambient acoustic events and then using signal processing to insert an anti-noise signal into the output of the device to cancel the ambient acoustic events.

Since the acoustic environment around personal audio devices, such as wireless telephones, can change dramatically, depending on the sources of noise that are present and the position of the device itself, it is desirable to adapt the noise canceling to take into account such environmental changes. However, the performance of an adaptive noise canceling system varies with how closely the transducer used to generate the output audio including noise-canceling information is coupled to the user's ear.

Therefore, it would be desirable to provide a personal audio device, including a wireless telephone, that provides noise cancellation in a variable acoustic environment and that can compensate for the quality of the coupling between the output transducer and the user's ear.

SUMMARY OF THE INVENTION

The above stated objective of providing a personal audio device providing noise cancellation in a variable acoustic environment and that compensates for the quality of coupling between the output transducer and the user's ear, is accomplished in a personal audio device, a method of operation, and an integrated circuit.

The personal audio device includes a housing, with a transducer mounted on the housing for reproducing an audio signal that includes both source audio for playback to a listener and an anti-noise signal for countering the effects of ambient audio sounds in an acoustic output of the transducer. A reference microphone is mounted on the housing to provide a reference microphone signal indicative of the ambient audio sounds. The personal audio device further includes an adaptive noise-canceling (ANC) processing circuit within the housing for adaptively generating an anti-noise signal from the reference microphone signal such that the anti-noise signal causes substantial cancellation of the ambient audio sounds. An error microphone is included for correcting for the electro-acoustic path from the output of the processing circuit through the transducer and to determine the degree of coupling between the user's ear and the transducer and a secondary path estimating adaptive filter is used to correct the error microphone signal for changes due to the acoustic path from the transducer to the error microphone. The ANC processing circuit monitors the response of the secondary path adaptive filter and optionally the error microphone signal to determine the pressure between the user's ear and the personal audio device. The ANC circuit then takes action to prevent the anti-noise signal from being undesirably/erroneously generated due to the phone being away from the user's ear (loosely coupled) or pressed too hard on the user's ear.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

The present invention encompasses noise canceling techniques and circuits that can be implemented in a personal audio device, such as a wireless telephone. The personal audio device includes an adaptive noise canceling (ANC) circuit that measures the ambient acoustic environment and generates a signal that is injected into the speaker (or other transducer) output to cancel ambient acoustic events. A reference microphone is provided to measure the ambient acoustic environment and an error microphone is included to measure the ambient audio and transducer output at the transducer, thus giving an indication of the effectiveness of the noise cancellation. However, depending on the contact pressure between the user's ear and the personal audio device, the ANC circuit may operate improperly and the anti-noise may be ineffective or even worsen the audibility of the audio information being presented to the user. The present invention provides mechanisms for determining the level of contact pressure between the device and the user's ear and taking action on the ANC circuits to avoid undesirable responses.

Figure 1:
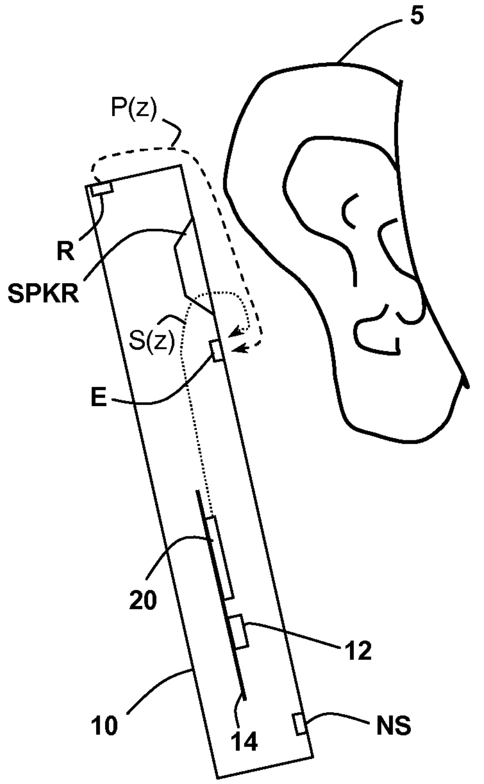
FIG. 1 is an illustration of a wireless telephone 10 in accordance with an embodiment of the present invention.

Referring now to FIG. 1, a wireless telephone 10 is illustrated in accordance with an embodiment of the present invention is shown in proximity to a human ear 5. Illustrated wireless telephone 10 is an example of a device in which techniques in accordance with embodiments of the invention may be employed, but it is understood that not all of the elements or configurations embodied in illustrated wireless telephone 10, or in the circuits depicted in subsequent illustrations, are required in order to practice the invention recited in the Claims. Wireless telephone 10 includes a transducer such as speaker SPKR that reproduces distant speech received by wireless telephone 10, along with other local audio event such as ringtones, stored audio program material, injection of near-end speech (i.e., the speech of the user of wireless telephone 10) to provide a balanced conversational perception, and other audio that requires reproduction by wireless telephone 10, such as sources from web-pages or other network communications received by wireless telephone 10 and audio indications such as battery low and other system event notifications. A near-speech microphone NS is provided to capture near-end speech, which is transmitted from wireless telephone 10 to the other conversation participant(s).

Wireless telephone 10 includes adaptive noise canceling (ANC) circuits and features that inject an anti-noise signal into speaker SPKR to improve intelligibility of the distant speech and other audio reproduced by speaker SPKR. A reference microphone R is provided for measuring the ambient acoustic environment, and is positioned away from the typical position of a user's mouth, so that the near-end speech is minimized in the signal produced by reference microphone R. A third microphone, error microphone E, is provided in order to further improve the ANC operation by providing a measure of the ambient audio combined with the audio reproduced by speaker SPKR close to ear 5, when wireless telephone 10 is in close proximity to ear 5. Exemplary circuit 14 within wireless telephone 10 includes an audio CODEC integrated circuit 20 that receives the signals from reference microphone R, near speech microphone NS and error microphone E and interfaces with other integrated circuits such as an RF integrated circuit 12 containing the wireless telephone transceiver. In other embodiments of the invention, the circuits and techniques disclosed herein may be incorporated in a single integrated circuit that contains control circuits and other functionality for implementing the entirety of the personal audio device, such as an MP3 player-on-a-chip integrated circuit.

In general, the ANC techniques of the present invention measure ambient acoustic events (as opposed to the output of speaker SPKR and/or the near-end speech) impinging on reference microphone R, and by also measuring the same ambient acoustic events impinging on error microphone E, the ANC processing circuits of illustrated wireless telephone 10 adapt an anti-noise signal generated from the output of reference microphone R to have a characteristic that minimizes the amplitude of the ambient acoustic events present at error microphone E. Since acoustic path P(z) extends from reference microphone R to error microphone E, the ANC circuits are essentially estimating acoustic path P(z) combined with removing effects of an electro-acoustic path S(z). Electro-acoustic path S(z) represents the response of the audio output circuits of CODEC IC 20 and the acoustic/electric transfer function of speaker SPKR including the coupling between speaker SPKR and error microphone E in the particular acoustic environment. S(z) is affected by the proximity and structure of ear 5 and other physical objects and human head structures that may be in proximity to wireless telephone 10, when wireless telephone is not firmly pressed to ear 5. While the illustrated wireless telephone 10 includes a two microphone ANC system with a third near speech microphone NS, some aspects of the present invention may be practiced in a system in accordance with other embodiments of the invention that do not include separate error and reference microphones, or yet other embodiments of the invention in which a wireless telephone uses near speech microphone NS to perform the function of the reference microphone R. Also, in personal audio devices designed only for audio playback, near speech microphone NS will generally not be included, and the near-speech signal paths in the circuits described in further detail below can be omitted, without changing the scope of the invention, other than to limit the options provided for input to the microphone covering detection schemes.

Figure 2:
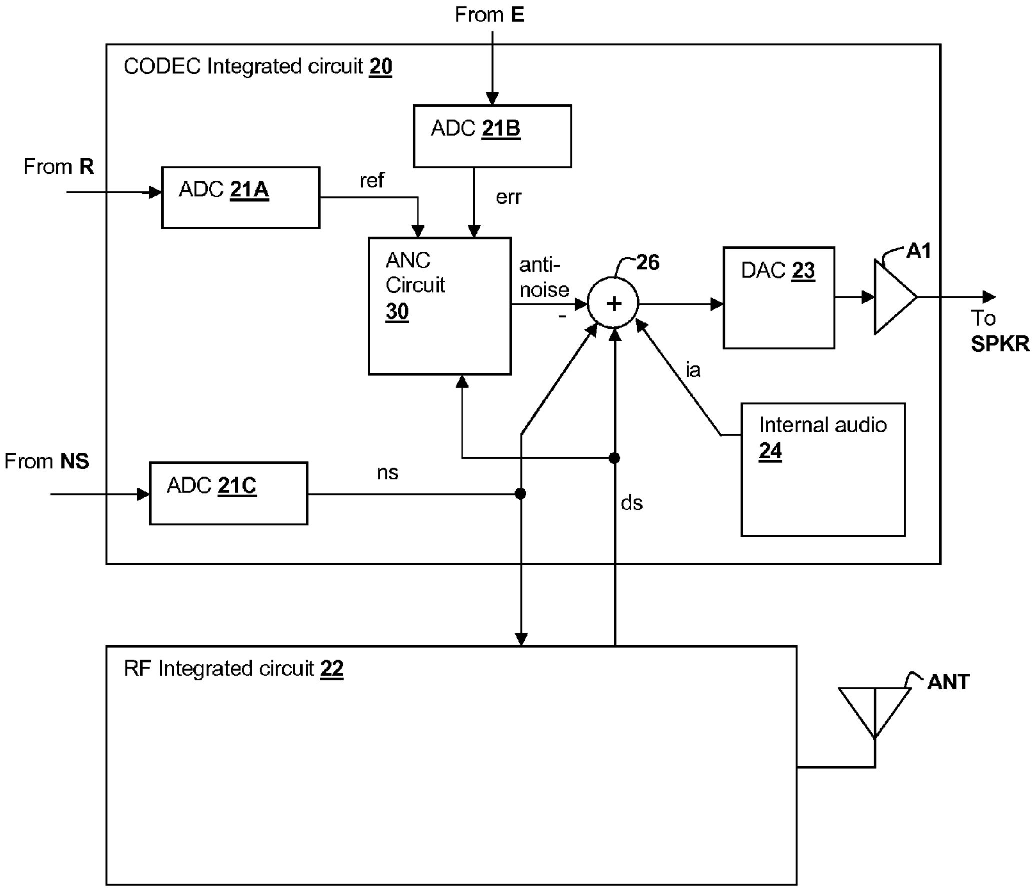
FIG. 2 is a block diagram of circuits within wireless telephone 10 in accordance with an embodiment of the present invention.

Referring now to FIG. 2, circuits within wireless telephone 10 are shown in a block diagram. CODEC integrated circuit 20 includes an analog-to-digital converter (ADC) 21A for receiving the reference microphone signal and generating a digital representation ref of the reference microphone signal, an ADC 21B for receiving the error microphone signal and generating a digital representation err of the error microphone signal, and an ADC 21C for receiving the near speech microphone signal and generating a digital representation ns of the error microphone signal. CODEC IC 20 generates an output for driving speaker SPKR from an amplifier A1, which amplifies the output of a digital-to-analog converter (DAC) 23 that receives the output of a combiner 26. Combiner 26 combines audio signals from internal audio sources 24, the anti-noise signal generated by ANC circuit 30, which by convention has the same polarity as the noise in reference microphone signal ref and is therefore subtracted by combiner 26, a portion of near speech signal ns so that the user of wireless telephone 10 hears their own voice in proper relation to downlink speech ds, which is received from radio frequency (RF) integrated circuit 22 and is also combined by combiner 26. Near speech signal ns is also provided to RF integrated circuit 22 and is transmitted as uplink speech to the service provider via antenna ANT.

Figure 3:
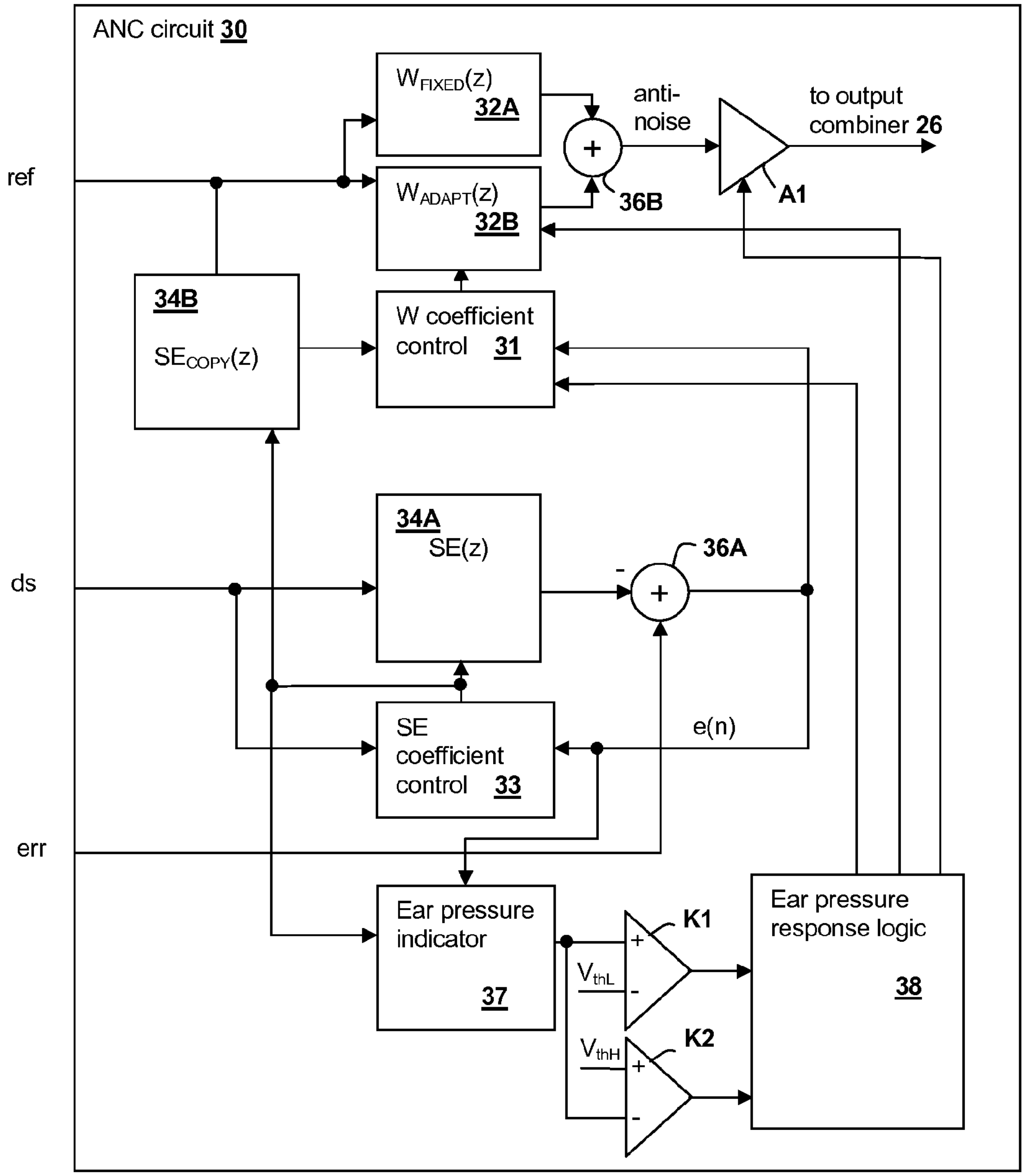
FIG. 3 is a block diagram depicting signal processing circuits and functional blocks within ANC circuit 30 of CODEC integrated circuit 20 of FIG. 2 in accordance with an embodiment of the present invention.

Referring now to FIG. 3, details of ANC circuit 30 are shown in accordance with an embodiment of the present invention. An adaptive filter formed from a fixed filter 32A having a response $W_{FIXED}(z)$ and an adaptive portion 32B having a response $W_{ADAPT}(z)$ with outputs summed by a combiner 36B receives reference microphone signal ref and under ideal circumstances, adapts its transfer function W(z) $=W_{FIXED}(z)+W_{ADAPT}(z)$ to generate the anti-noise signal, which is provided to an output combiner that combines the anti-noise signal with the audio to be reproduced by the transducer, as exemplified by combiner 26 of FIG. 2. The response of W(z) adapts to estimate P(z)/S(z), which is the ideal response for the anti-noise signal under ideal operating conditions. A controllable amplifier circuit A1 mutes or attenuates the anti-noise signal under certain non-ideal conditions as described in further detail below, when the anti-noise signal is expected to be ineffective or erroneous due to a lack of seal between the user's ear and wireless telephone 10. The coefficients of adaptive filter 32B are controlled by a W coefficient control block 31 that uses a correlation of two signals to determine the response of adaptive filter 32B, which generally minimizes the energy of the error, in a least-mean squares sense, between those components of reference microphone signal ref that are present in error microphone signal err. The signals compared by W coefficient control block 31 are the reference microphone signal ref as shaped by a copy of an estimate $SE_{COPY}(z)$ of the response of path S(z) provided by filter 34B and an error signal e(n) formed by subtracting a modified portion of downlink audio signal ds from error microphone signal err. By transforming reference microphone signal ref with a copy of the estimate of the response of path S(z), estimate $SE_{COPY}(z)$, and adapting adaptive filter 32B to minimize the correlation between the resultant signal and the error microphone signal err, adaptive filter 32B adapts to the desired response of P(z)/S(z)−$W_{FIXED}$(z), and thus response W(z) adapts to P(z)/S(z), resulting in a noise-canceling error that is ideally white noise. As mentioned above, the signal compared to the output of filter 34B by W coefficient control block 31 adds to the error microphone signal an inverted amount of downlink audio signal ds that has been processed by filter response SE(z), of which response $SE_{COPY}$(z) is a copy. By injecting an inverted amount of downlink audio signal ds, adaptive filter 32B is prevented from adapting to the relatively large amount of downlink audio present in error microphone signal err and by transforming that inverted copy of downlink audio signal ds with the estimate of the response of path S(z), the downlink audio that is removed from error microphone signal err before comparison should match the expected version of downlink audio signal ds reproduced at error microphone signal err, since the electrical and acoustical path of S(z) is the path taken by downlink audio signal ds to arrive at error microphone E. Filter 34B is not an adaptive filter, per se, but has an adjustable response that is tuned to match the response of adaptive filter 34A, so that the response of filter 34B tracks the adapting of adaptive filter 34A.

To implement the above, adaptive filter 34A has coefficients controlled by SE coefficient control block 33, which compares downlink audio signal ds and error microphone signal err after removal of the above-described filtered downlink audio signal ds, that has been filtered by adaptive filter 34A to represent the expected downlink audio delivered to error microphone E, and which is removed from the output of adaptive filter 34A by a combiner 36A. SE coefficient control block 33 correlates the actual downlink speech signal ds with the components of downlink audio signal ds that are present in error microphone signal err. Adaptive filter 34A is thereby adapted to generate a signal from downlink audio signal ds (and optionally, the anti-noise signal combined by combiner 36B during muting conditions as described above), that when subtracted from error microphone signal err, contains the content of error microphone signal err that is not due to downlink audio signal ds. As will be described in further detail below, the overall energy of the error signal normalized to the overall energy of the response SE(z) is related to the quality of the seal between the user's ear and wireless telephone 10. An ear pressure indicator computation block 37 determines the ratio between E|e(n)|, which is the energy of the error signal generated by combiner 36 and the overall magnitude of the response of SE(z): $\Sigma|SE_n(z)|$. Ear pressure indication $E|e(n)|/\Sigma|SE_n(z)|$ is only one possible function of e(n) and $SE_n(z)$ that may be used to yield a measure of ear pressure. For example, $\Sigma|SE_n(z)|$ or $\Sigma\ SE_n(z)^2$ which are functions of only SE(z) can alternatively be used, since response SE(z) changes with ear pressure. A comparator K1 compares the output of computation block 37 with a low pressure threshold $V_{thL}$. If $E|e(n)|/\Sigma|SE_n(z)|$ is above the threshold, indicating that ear pressure is below the normal operating range (e.g., wireless telephone 10 is off of the user's ear) then ear pressure response logic is signaled to take action to prevent generation of undesirable anti-noise at the user's ear 5. Similarly, a comparator K2 compares the output of computation block with a high pressure threshold $V_{thH}$ and if $E|e(n)|/\Sigma|SE_n(z)|$ is below the threshold, indicating that ear pressure is above the normal operating range (e.g., wireless telephone 10 is pressed hard onto the user's ear) then ear pressure response logic is also signaled to take action to prevent generation of undesirable anti-noise at the user's ear 5.

Figure 4:
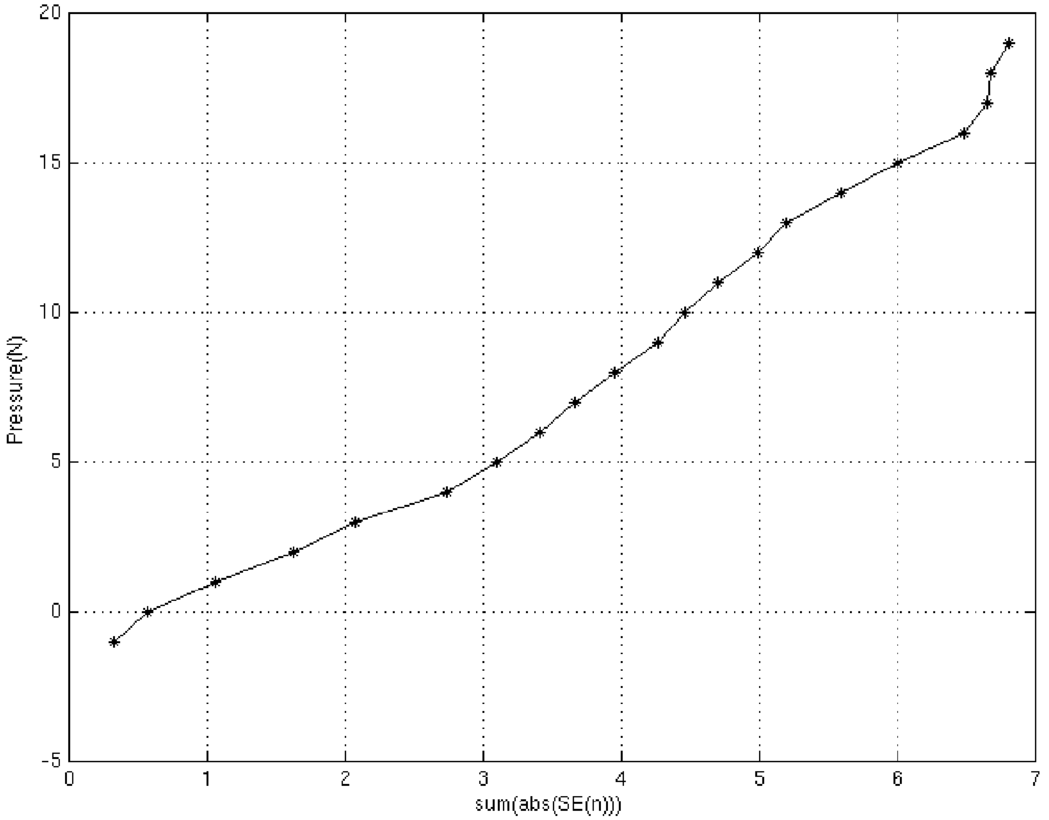
FIG. 4 is a graph illustrating the relationship between pressure between a user's ear (quality of transducer seal) and wireless telephone 10 to the overall energy of secondary path response estimate SE(z).

Referring now to FIG. 4, the relationship between the overall magnitude of the response of SE(z), $\Sigma|SE_n(z)|$ is shown vs. pressure in Newtons, between wireless telephone 10 and a user's ear. As illustrated, as the pressure is increased between wireless telephone 10 and the user's ear 5, response SE(z) increases in magnitude, which indicates an improved electro-acoustic path S(z), which is a measure of a degree of coupling between speaker SPKR and error microphone E as described above, and thus the degree of coupling between the user's ear 5 and speaker SPKR. A higher degree of coupling between the user's ear 5 and speaker SPKR is indicated when response SE(z) increases in magnitude, and conversely, a lower degree of coupling between the user's ear and speaker SPKR is indicated when response SE(z) decreases in magnitude. Since adaptive filter 32B adapts to the desired response of P(z)/S(z), as ear pressure is increased and response SE(z) increases in energy, less anti-noise is required and thus less is generated. Conversely, as the pressure between the ear and wireless telephone 10 decreases, the anti-noise signal will increase in energy and may not be suitable for use, since the user's ear is no longer well-coupled to transducer SPKR and error microphone E.

Figure 5:
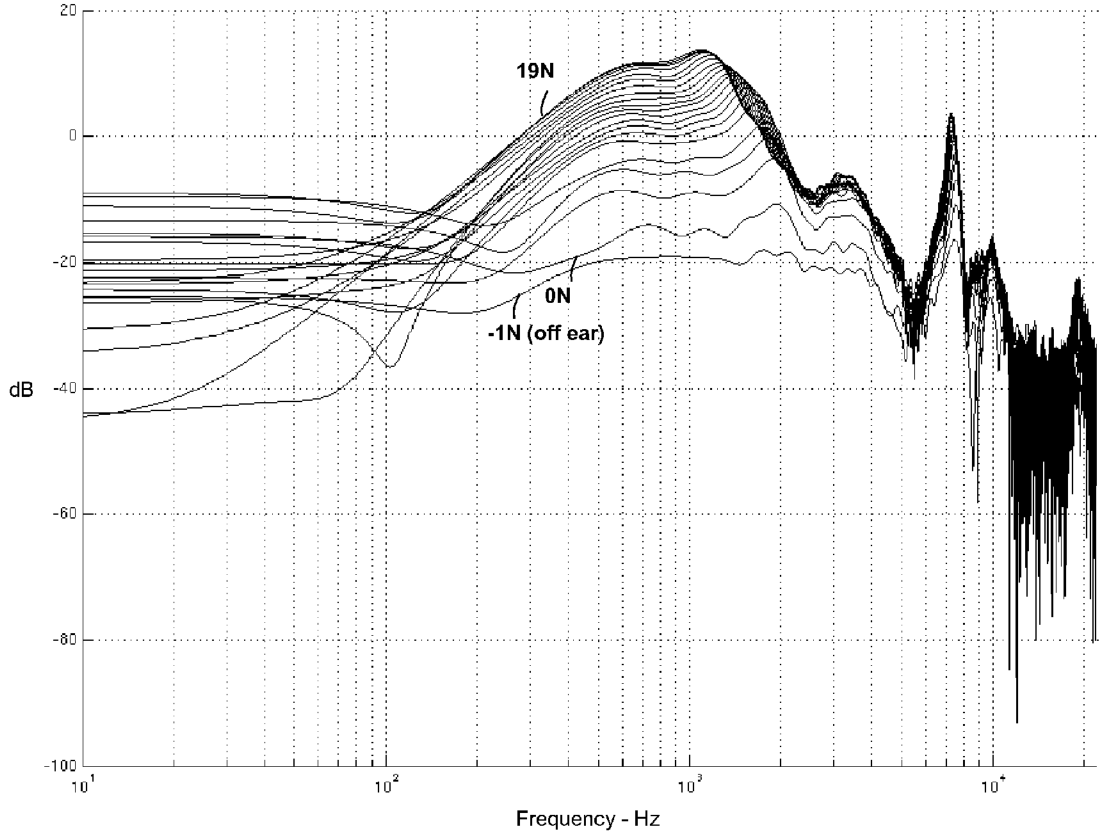
FIG. 5 is a graph illustrating the frequency response of a secondary path response estimate SE(z) for different amounts of pressure between a user's ear and a wireless telephone 10.

Referring now to FIG. 5, the variation of response SE(z) with frequency for different levels of ear pressure is shown. As illustrated in FIG. 4, as the pressure is increased between wireless telephone 10 and the user's ear 5, response SE(z) increases in magnitude in the middle frequency ranges of the graph, which correspond to frequencies at which most of the energy in speech is located. The graphs depicted in FIGS. 4-5 are determined for individual wireless telephone designs using either a computer model, or a mock-up of a simulated user's head that allows adjustment of contact pressure between the head, which may also have a measurement microphone in simulated ear canal, and wireless telephone 10. In general, ANC only operates properly when there is a reasonable degree of coupling between the user's ear 5, transducer SPKR, and error microphone E. Since transducer SPKR will only be able to generate a certain amount of output level, e.g., 80 dB SPL in a closed cavity, once wireless telephone 10 is no longer in contact with the user's ear 5, the anti-noise signal is generally ineffective and in many circumstances should be muted. The lower threshold in this case may be, for example, a response SE(z) that indicates an ear pressure of 4N, or less. On the opposite end of the pressure variation realm, tight contact between the user's ear 5 and wireless telephone 10 provides attenuation of higher-frequency energy (e.g., frequencies from 2kHZ to 5 kHz), which can cause noise boost due to response W(z) not being able to adapt to the attenuated condition of the higher frequencies, and when the ear pressure is increased, the anti-noise signal is not adapted to cancel energies at the higher frequencies. Therefore, response $W_{ADAPT}$(z) should be reset to a predetermined value and adaptation of response $W_{ADAPT}$(z) is frozen, i.e., the coefficients of response $W_{ADAPT}$(z) are held constant at the predetermined values. The upper threshold in this case may be, for example, a response SE(z) that indicates an ear pressure of 15N, or greater. Alternatively, the overall level of the anti-noise signal can be attenuated, or a leakage of response $W_{ADAPT}$(z) of adaptive filter 32B increased. Leakage of response $W_{ADAPT}$(z) of adaptive filter 32B is provided by having the coefficients of response $W_{ADAPT}$(z) return to a flat frequency response (or alternatively a fixed frequency response, e.g. in implementations having only a single adaptive filter stage without $W_{FIXED}$(z) providing the predetermined response).

When comparator K1 in the circuit of FIG. 3 indicates that the degree of coupling between the user's ear and wireless telephone has been reduced below a lower threshold, indicating a degree of coupling below the normal operating range, the following actions will be taken by ear pressure response logic 38:

1) Stop adaptation of W coefficient control 31

2) Mute the anti-noise signal by disabling amplifier A1

When comparator K2 in the circuit of FIG. 3 indicates that the coupling between the user's ear and wireless telephone has increased above an upper threshold, indicating a degree of coupling above the normal operating range, the following actions will be taken by ear pressure response logic 38:

1) Increase leakage of W coefficient control 31 or reset response $W_{ADAPT}(z)$ and freeze adaptation of response $W_{ADAPT}(z)$. As an alternative, the value produced by computation block 37 can be a multi-valued or continuous indication of different ear pressure levels, and the actions above can be replaced by applying an attenuation factor to the anti-noise signal in conformity with the level of ear pressure, so that when the ear pressure passes out of the normal operating range the anti-noise signal level is also attenuated by lowering the gain of amplifier A1. In one embodiment of the invention, response $W_{FIXED}(z)$ of fixed filter 32A is trained for maximum ear pressure, i.e., set to the appropriate response for to the maximum level of ear pressure (perfect seal). Then, the adaptive response of adaptive filter 32B, response $W_{ADAPT}(z)$, is allowed to vary with ear pressure changes, up to the point that contact with the ear is minimal (no seal), at which point the adapting of response W(z) is halted and the anti-noise signal is muted, or the pressure on the ear is over the maximum pressure, at which point response $W_{ADAPT}(z)$ is reset and adaptation of response $W_{ADAPT}(z)$ is frozen, or the leakage is increased.

Figure 6:
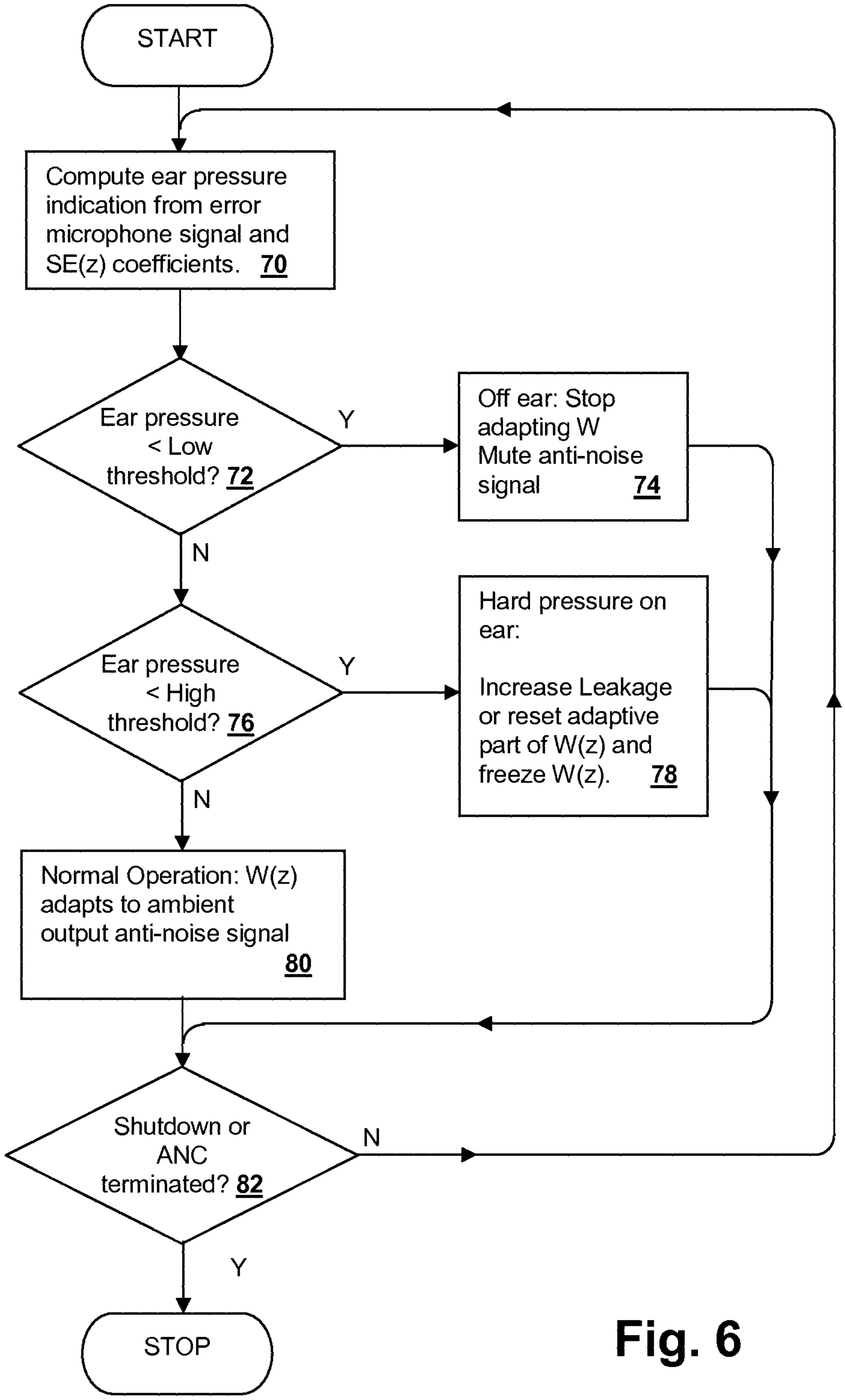
FIG. 6 is a flowchart depicting a method in accordance with an embodiment of the present invention.

Referring now to FIG. 6, a method in accordance with an embodiment of the present invention is depicted in a flowchart. An indication of ear pressure is computed from the error microphone signal and response SE(z) coefficients as described above (step 70). If the ear pressure is less than the low threshold (decision 72), then wireless telephone is in the off-ear condition and the ANC system stops adapting response W(z) and mutes the anti-noise signal (step 74). Alternatively, if the ear pressure is greater than the high threshold (decision 76), then wireless telephone 10 is pressed hard to the user's ear and leakage of response W(z) response is increased or the adaptive portion of response W(z) is reset and frozen (step 78). Otherwise, if the ear pressure indication lies within the normal operating range ("No" to both decision 72 and decision 76)$_5$ response W(z) adapts to the ambient audio environment and the anti-noise signal is output (step 80). Until the ANC scheme is terminated or wireless telephone 10 is shut down (decision 82), the process of steps 70-82 are repeated.

Figure 7:
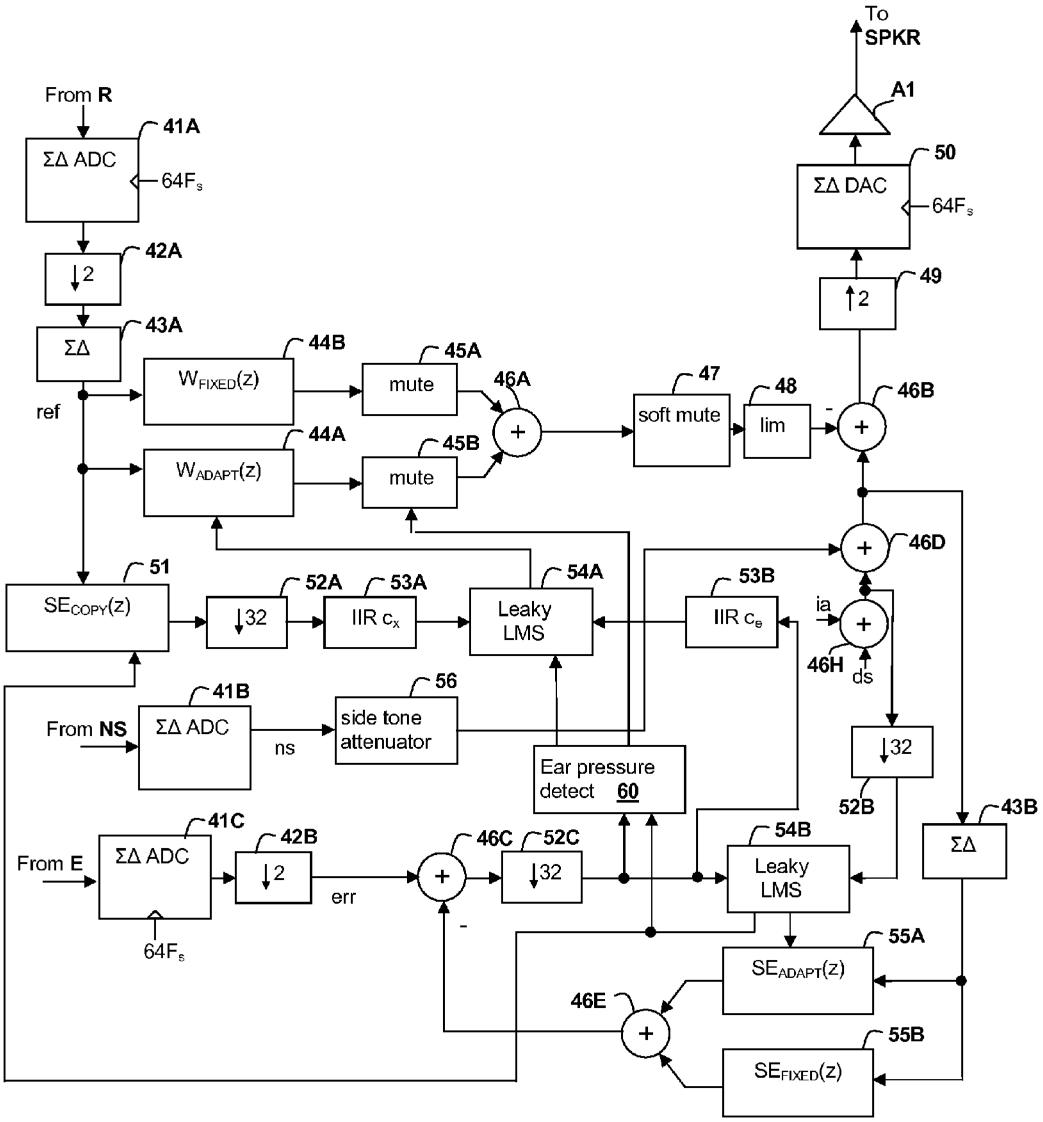
FIG. 7 is a block diagram depicting signal processing circuits and functional blocks within an integrated circuit in accordance with an embodiment of the present invention.

Referring now to FIG. 7, a block diagram of an ANC system is shown for illustrating ANC techniques in accordance an embodiment of the invention, as may be implemented within CODEC integrated circuit 20. Reference microphone signal ref is generated by a delta-sigma ADC 41A that operates at 64 times oversampling and the output of which is decimated by a factor of two by a decimator 42A to yield a 32 times oversampled signal. A delta-sigma shaper 43A spreads the energy of images outside of bands in which a resultant response of a parallel pair of filter stages 44A and 44B will have significant response. Filter stage 44B has a fixed response $W_{FIXED}(z)$ that is generally predetermined to provide a starting point at the estimate of P(z)/S(z) for the particular design of wireless telephone 10 for a typical user. An adaptive portion $W_{ADAPT}(z)$ of the response of the estimate of P(z)/S(z) is provided by adaptive filter stage 44A, which is controlled by a leaky least-means-squared (LMS) coefficient controller 54A. Leaky LMS coefficient controller 54A is leaky in that the response normalizes to flat or otherwise predetermined response over time when no error input is provided to cause leaky LMS coefficient controller 54A to adapt. Providing a leaky controller prevents long-term instabilities that might arise under certain environmental conditions, and in general makes the system more robust against particular sensitivities of the ANC response. As in the system of FIG. 3, an ear pressure detection circuit 60 detects when the ear pressure indication is out of the normal operating range and takes action to prevent the anti-noise signal from being output and adaptive filter 44A from adapting to an incorrect response (off-ear) or increases the leakage of adaptive filter 44A or resets adaptive filter 44A to a predetermined response (hard pressure on ear) and freezes adaptation.

In the system depicted in FIG. 7, the reference microphone signal is filtered by a copy $SE_{COPY}(z)$ of the estimate of the response of path S(z), by a filter 51 that has a response $SE_{COPY}(z)$, the output of which is decimated by a factor of 32 by a decimator 52A to yield a baseband audio signal that is provided, through an infinite impulse response (IIR) filter 53A to leaky LMS 54A. Filter 51 is not an adaptive filter, per se, but has an adjustable response that is tuned to match the combined response of filter stages 55A and 55B, so that the response of filter 51 tracks the adapting of response SE(z). The error microphone signal err is generated by a delta-sigma ADC 41C that operates at 64 times oversampling and the output of which is decimated by a factor of two by a decimator 42B to yield a 32 times oversampled signal. As in the system of FIG. 3, an amount of downlink audio ds that has been filtered by an adaptive filter to apply response S(z) is removed from error microphone signal err by a combiner 46C, the output of which is decimated by a factor of 32 by a decimator 52C to yield a baseband audio signal that is provided, through an infinite impulse response (IIR) filter 53B to leaky LMS 54A. Response S(z) is produced by another parallel set of filter stages 55A and 55B, one of which, filter stage 55B has fixed response $SE_{FIXED}(z)$, and the other of which, filter stage 55A has an adaptive response $SE_{ADAPT}(z)$ controlled by leaky LMS coefficient controller MB. The outputs of filter stages 55A and 55B are combined by a combiner 46E. Similar to the implementation of filter response W(z) described above, response $SE_{FIXED}(z)$ is generally a predetermined response known to provide a suitable starting point under various operating conditions for electrical/acoustical path S(z). Filter 51 is a copy of adaptive filter 55A/55B, but is not itself and adaptive filter, i.e., filter 51 does not separately adapt in response to its own output, and filter 51 can be implemented using a single stage or a dual stage. A separate control value is provided in the system of FIG. 7 to control the response of filter 51, which is shown as a single adaptive filter stage. However, filter 51 could alternatively be implemented using two parallel stages and the same control value used to control adaptive filter stage 55A could then be used to control the adjustable filter portion in the implementation of filter 51. The inputs to leaky LMS control block MB are also at baseband, provided by decimating a combination of downlink audio signal ds and internal audio ia, generated by a combiner 46H, by a decimator 52B that decimates by a factor of 32, and another input is provided by decimating the output of a combiner 46C that has removed the signal generated from the combined outputs of adaptive filter stage 55A and filter stage 55B that are combined by another combiner 46E. The output of combiner 46C represents error microphone signal err with the components due to downlink audio signal ds removed, which is provided to LMS control block MB after decimation by decimator 52C.

The other input to LMS control block 54B is the baseband signal produced by decimator 52B.

The above arrangement of baseband and oversampled signaling provides for simplified control and reduced power consumed in the adaptive control blocks, such as leaky LMS controllers 54A and 54B, while providing the tap flexibility afforded by implementing adaptive filter stages 44A-44B, 55A-55B and filter 51 at the oversampled rates. The remainder of the system of FIG. 7 includes combiner 46H that combines downlink audio ds with internal audio ia, the output of which is provided to the input of a combiner 46D that adds a portion of near-end microphone signal ns that has been generated by sigma-delta ADC 41B and filtered by a sidetone attenuator 56 to prevent feedback conditions. The output of combiner 46D is shaped by a sigma-delta shaper 43B that provides inputs to filter stages 55A and 55B that has been shaped to shift images outside of bands where filter stages 55A and 55B will have significant response.

In accordance with an embodiment of the invention, the output of combiner 46D is also combined with the output of adaptive filter stages 44A-44B that have been processed by a control chain that includes a corresponding hard mute block 45A, 45B for each of the filter stages, a combiner 46A that combines the outputs of hard mute blocks 45A, 45B, a soft mute 47 and then a soft limiter 48 to produce the anti-noise signal that is subtracted by a combiner 46B with the source audio output of combiner 46D. The output of combiner 46B is interpolated up by a factor of two by an interpolator 49 and then reproduced by a sigma-delta DAC 50 operated at the 64× oversampling rate. The output of DAC 50 is provided to amplifier A1, which generates the signal delivered to speaker SPKR.

Each or some of the elements in the system of FIG. 7, as well in as the exemplary circuits of FIG. 2 and FIG. 3, can be implemented directly in logic, or by a processor such as a digital signal processing (DSP) core executing program instructions that perform operations such as the adaptive filtering and LMS coefficient computations. While the DAC and ADC stages are generally implemented with dedicated mixed-signal circuits, the architecture of the ANC system of the present invention will generally lend itself to a hybrid approach in which logic may be, for example, used in the highly oversampled sections of the design, while program code or microcode-driven processing elements are chosen for the more complex, but lower rate operations such as computing the taps for the adaptive filters and/or responding to detected changes in ear pressure as described herein.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

a reference microphone mounted on the housing for providing a reference microphone signal indicative of the ambient audio sounds;

an error microphone mounted on the housing in proximity to the transducer for providing an error microphone signal indicative of the acoustic output of the transducer; and a processing circuit that implements a first adaptive filter having a response that shapes the anti-noise signal to reduce the presence of the ambient audio sounds heard by the listener, wherein the first adaptive filter filters the reference microphone signal to generate the anti-noise signal, wherein the processing circuit implements a secondary path adaptive filter having a secondary path response that shapes the source audio and a combiner that removes the shaped source audio from the error microphone signal to provide an error signal indicative of the combined anti-noise signal and ambient audio sounds delivered to the listener, wherein the processing circuit adapts the response of the first adaptive filter to minimize the error signal, wherein the processing circuit determines a degree of coupling between the transducer and an ear of the listener and detects a change in the degree of coupling by comparing a value of an ear pressure indication computed from the secondary path response to a predetermined threshold, and wherein the processing circuit alters the response of the first adaptive filter in response to the value of the ear pressure indication crossing the predetermined threshold.

2. The personal audio device of claim 1, wherein the processing circuit alters the response of the first adaptive filter by forcing the response of the first adaptive filter to a predetermined response in response to determining that the degree of coupling is greater than an upper threshold value.

3. The personal audio device of claim 2, wherein the predetermined response is a response that is trained to cancel the presence of the ambient audio sounds heard by the listener when the degree of coupling is greater than the upper threshold value.

4. The personal audio device of claim 2, wherein an adaptive control of the response of the first adaptive filter has a leakage characteristic that restores the response of the first adaptive filter to the predetermined response at an adjustable rate of change, and wherein the processing circuit increases the adjustable rate of change in response to determining the degree of coupling is greater than the upper threshold value.

5. The personal audio device of claim 1, wherein the processing circuit mutes the anti-noise signal in response to determining that the degree of coupling is lower than a lower threshold value.

6. The personal audio device of claim 5, wherein the processing circuit stops adaptation of the response of the first adaptive filter in response to determining that the degree of coupling is lower than the lower threshold value.

7. The personal audio device of claim 5, wherein the processing circuit alters the response of the first adaptive filter by forcing the response of the first adaptive filter to a predetermined response in response to determining that the ear of the listener and the transducer to determining that the degree of coupling is greater than an upper threshold value.

8. The personal audio device of claim 7, wherein an adaptive control of the response of the first adaptive filter has a leakage characteristic that restores the response of the first adaptive filter to the predetermined response at an adjustable rate of change, and wherein the processing circuit increases the adjustable rate of change in response to determining that the degree of coupling is greater than the upper threshold value.

9. The personal audio device of claim 1, wherein the processing circuit determines the degree of coupling between the transducer and the ear of the listener from a magnitude of the error signal weighted by an inverse of a peak magnitude of the secondary path response of the secondary path adaptive filter, wherein an decrease in the magnitude of the error signal weighted by the inverse of the peak magnitude of the secondary path response of the secondary path adaptive filter indicates a greater degree of coupling between the transducer and the ear of the listener.

10. The personal audio device of claim 1, wherein the processing circuit determines the change in the degree of coupling between the transducer and the ear of the listener by comparing an indication of a peak magnitude of the secondary path response of the secondary path adaptive filter to a threshold value, wherein an increase in the peak magnitude of the secondary path response of the secondary path adaptive filter indicates a greater degree of coupling between the transducer and the ear of the listener.

11. A method of canceling ambient audio sounds in the proximity of a transducer of a personal audio device, the method comprising:

first measuring ambient audio sounds with a reference microphone;

second measuring an output of the transducer with an error microphone;

adaptively generating an anti-noise signal from a result of the first measuring for countering the effects of ambient audio sounds at an acoustic output of the transducer by adapting a response of a first adaptive filter that filters an output of the reference microphone;

filtering the reference microphone signal to generate the anti-noise signal, shaping the source audio with a secondary path response;

removing the shaped source audio from the error microphone signal to provide an error signal indicative of the combined anti-noise signal and ambient audio sounds delivered to the listener;

adapting the response of the first adaptive filter to minimize the error signal;

combining the anti-noise signal with a source audio signal to generate an audio signal provided to the transducer;

determining a degree of coupling between the transducer and an ear of the listener;

detecting a change in the degree of coupling by comparing a value of an ear pressure indication computed from the secondary path response to a predetermined threshold; and altering the response of the first adaptive filter in response to the value of the ear pressure indication crossing the predetermined threshold.

12. The method of claim 11, wherein the altering alters the response of the first adaptive filter by forcing the response of the first adaptive filter to a predetermined response in response to determining that the degree of coupling is greater than an upper threshold.

13. The method of claim 12, wherein the predetermined response is a response that is trained to cancel the presence of the ambient audio sounds heard by the listener in response to determining that the degree of coupling is greater than an upper threshold.

14. The method of claim 12, wherein an adaptive control of the response of the first adaptive filter has a leakage characteristic that restores the response of the first adaptive filter to a predetermined response at an adjustable rate of change, and wherein the altering increases the adjustable rate of change in response to determining that the degree of coupling is less than a lower threshold.

15. The method of claim 12, further comprising muting the anti-noise signal in response to determining that the degree of coupling is less than a lower threshold.

16. The method of claim 15, wherein the altering stops adaptation of the response of the first adaptive filter in response to determining that the degree of coupling is less than the lower threshold.

17. The method of claim 15, wherein the altering alters the response of the first adaptive filter by forcing the response of the first adaptive filter to a predetermined response in response to determining that the degree of coupling is greater than an upper threshold.

18. The method of claim 17, wherein an adaptive control of the response of the first adaptive filter has a leakage characteristic that restores the response of the first adaptive filter to a predetermined response at an adjustable rate of change, and wherein the altering increases the adjustable rate of change in response to determining the degree of coupling is less than the lower threshold.

19. The method of claim 11, wherein the determining determines the degree of coupling between the transducer and the ear of the listener from a magnitude of the error signal weighted by an inverse of a peak magnitude of the secondary path response of the secondary path adaptive filter, wherein a decrease in the magnitude of the error signal weighted by the inverse of the peak magnitude of the secondary path response of the secondary path adaptive filter indicates a greater degree of coupling between the transducer and the ear of the listener.

20. The method of claim 11, wherein the determining determines the change in the degree of coupling between the transducer and the ear of the listener from an indication of a peak magnitude of the secondary path response of the secondary path adaptive filter wherein an increase in the peak magnitude of the secondary path response of the secondary path adaptive filter indicates a greater degree of coupling between the transducer and the ear of the listener.

21. An integrated circuit for implementing at least a portion of a personal audio device, comprising:

an output for providing a signal to a transducer including both source audio for playback to a listener and an anti-noise signal for countering the effects of ambient audio sounds in an acoustic output of the transducer;

a reference microphone input for receiving a reference microphone signal indicative of the ambient audio sounds;

an error microphone input for receiving an error microphone signal indicative of the output of the transducer; and a processing circuit that implements a first adaptive filter having a response that shapes the anti-noise signal to reduce the presence of the ambient audio sounds heard by the listener listener, wherein the first adaptive filter filters the reference microphone signal to generate the anti-noise signal, wherein the processing circuit implements a secondary path adaptive filter having a secondary path response that shapes the source audio and a combiner that removes the shaped source audio from the error microphone signal to provide an error signal indicative of the combined anti-noise signal and ambient audio sounds delivered to the listener, wherein the processing circuit adapts the response of the first adaptive filter to minimize the error signal, wherein the processing circuit determines a degree of coupling between the transducer and an ear of the listener and detects a change in the degree of coupling by comparing a value of an ear pressure indication computed from the secondary path response to a predetermined threshold, and wherein the processing circuit alters the response of the first adaptive filter in response to the value of the ear pressure indication crossing the predetermined threshold.

22. The integrated circuit of claim 21, wherein the processing circuit alters the response of the first adaptive filter by forcing the response of the first adaptive filter to a predetermined response in response to determining that the degree of coupling is greater than an upper threshold.

23. The integrated circuit of claim 22, wherein the predetermined response is a response that is trained to cancel the presence of the ambient audio sounds heard by the listener in response to determining that the degree of coupling is greater than the upper threshold.

24. The integrated circuit of claim 22, wherein an adaptive control of the response of the first adaptive filter has a leakage characteristic that restores the response of the first adaptive filter to a predetermined response at an adjustable rate of change, and wherein the processing circuit increases the adjustable rate of change in response to determining that the degree of coupling is greater than the upper threshold.

25. The integrated circuit of claim 24, wherein the processing circuit mutes the anti-noise signal in response to determining that when the degree of coupling is less than a lower threshold.

26. The integrated circuit of claim 25, wherein the processing circuit stops adaptation of the response of the first adaptive filter in response to determining that the degree of coupling is less than the lower threshold.

27. The integrated circuit of claim 25, wherein the processing circuit alters the response of the first adaptive filter by forcing the response of the first adaptive filter to a predetermined response in response to determining that the degree of coupling is greater than an upper threshold.

28. The integrated circuit of claim 27, wherein an adaptive control of the response of the first adaptive filter has a leakage characteristic that restores the response of the first adaptive filter to the predetermined response at an adjustable rate of change, and wherein the processing circuit increases the adjustable rate of change in response to determining that the degree of coupling is greater than the upper threshold.

29. The integrated circuit of claim 21, wherein the processing circuit determines the degree of coupling between the transducer and the ear of the listener from a magnitude of the error signal weighted by an inverse of a peak magnitude of the secondary path response of the secondary path adaptive filter, wherein an decrease in the magnitude of the error signal weighted by the inverse of the peak magnitude of the secondary path response of the secondary path adaptive filter indicates a greater degree of coupling between the transducer and the ear of the listener.

30. The integrated circuit of claim 21, wherein the processing circuit determines the change in the degree of coupling between the transducer and the ear of the listener by comparing an indication of a peak magnitude of the secondary path response of the secondary path adaptive filter to a threshold value, wherein an increase in the peak magnitude of the secondary path response of the secondary path adaptive filter indicates a greater degree of coupling between the transducer and the ear of the listener.

* * * * *

UNITED STATES PATENT AND TRADEMARK OFFICE

CERTIFICATE OF CORRECTION

PATENT NO. : 8,908,877 B2
APPLICATION NO. : 13/310380
DATED : December 9, 2014
INVENTOR(S) : Abdollahzadeh Milani et al.

It is certified that error appears in the above-identified patent and that said Letters Patent is hereby corrected as shown below:

In the Claims

Column 12, line 1, claim 15, the claim reference numeral ‘12’ should read --11--.

Signed and Sealed this
Twenty-second Day of September, 2015

Michelle K. Lee
*Director of the United States Patent and Trademark Office*